United States Patent
Simon et al.

(10) Patent No.: US 10,602,702 B2
(45) Date of Patent: Mar. 31, 2020

(54) CATNIP CULTIVAR 'CR9'

(71) Applicant: Rutgers, the State University of New Jersey, New Brunswick, NJ (US)

(72) Inventors: James E. Simon, Princeton, NJ (US); William Reichert, Branchburg, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 410 days.

(21) Appl. No.: 15/338,014

(22) Filed: Oct. 28, 2016

(65) Prior Publication Data

US 2018/0116144 A1    May 3, 2018

(51) Int. Cl.
*A01H 6/50* (2018.01)
*A01H 5/02* (2018.01)

(52) U.S. Cl.
CPC .................. *A01H 6/50* (2018.05); *A01H 5/02* (2013.01)

(58) Field of Classification Search
CPC ....................................................... A01H 6/50
See application file for complete search history.

(56) References Cited

U.S. PATENT DOCUMENTS

| | | |
|---|---|---|
| 2004/0197362 A1 | 10/2004 | Wagner |
| 2016/0183432 P1 | 6/2016 | Ganzke et al. |
| 2019/0183082 A1 | 6/2019 | Simon et al. |

FOREIGN PATENT DOCUMENTS

| | | |
|---|---|---|
| WO | WO/2003/086069 | 10/2003 |
| WO | WO 2018/106946 | 6/2018 |

OTHER PUBLICATIONS

Catnip as a Source of Essential Oils Issues In New Crops and New Uses, pp. 311-315 J. Janick and A. Whipkey editors ASHS Press, Alexandria, VA (Year: 2007).*
Schultz et al, Environmental Entomology vol. 33, No. 6, pp. 1562-1569 (Year: 2004).*
Lee et al, Scientific Research and Essays vol. 5(10): 1122-1126 (Year: 2010).*
Birkett et al, Phytochemistry vol. 62, pp. 651-656 (Year: 2003).*
Johnson et al, Plant Disease 84(3): 235-238 (Year: 2000).*
Chauhan et al.. "Effect of catnip oils and its major components on the Formosan subterranean termite *Coptotermes formosanus*," *Biopestic Int*, 2:137-143, 2006.
Chauhan et al., "A field bioassay to evaluate potential spatial repellents against natural mosquito populations," *J Am Mosq Control Assoc*, 28:301-306, 2012.
Gkinis et al., "Chemical composition and biological activity of *Nepeta pamassica* oils and isolated nepetalactones," *Z Naturforsch C*, 58C:681-686, 2003.
McElvain et al., "The constituents of the volatile oil of catnip. I. Nepetalic acid, nepetalactone and related compounds," *J Am Chem Soc*, 63:1558-1563, 1941.
Park et al., "Catnip as a source of essential oils," In: Issues in New Crops and New Uses, Janick, J and A. Whipkey (eds.), 311-315, 2007.
Ulrich et al., "Comparison of contact and spatial repellency of catnip oil and N,N-Diethyl-3-methylbenzamide (Deet) against mosquitoes," *J Med Entomol*, 42:306-311, 2005.
Zhu et al., "Nepetalactones from essential oil of *Nepeta cataria* represent a stable fly feeding and oviposition repellent," *Med Vet Entomol*, 26:131-138, 2012.

* cited by examiner

*Primary Examiner* — David H Kruse
(74) *Attorney, Agent, or Firm* — Dentons US LLP

(57) ABSTRACT

The invention provides seed and plants of catnip hybrid 'CR9'. The invention thus relates to the plants, seeds, and tissue cultures of catnip hybrid 'CR9', and to methods for producing a catnip plant of the present invention by crossing such plants with themselves or with another catnip plant, such as a plant of another genotype, variety, or cultivar. The invention further relates to seeds and plants produced by such crossing. The invention further relates to parts of such plants.

23 Claims, 6 Drawing Sheets

CATNIP CULTIVAR 'CR9'

FIELD OF THE INVENTION

The present invention relates to the field of plant breeding and, more specifically, to the development of a new highly aromatic catnip cultivar designated 'CR9'.

BACKGROUND OF THE INVENTION

Catnip, (*Nepeta cataria*, Fam. Lamiaceae), an aromatic herb from southwestern Asia, is best known for causing a euphoric effect on domestic cats and other members of the feline family due to nepetalactone, a volatile compound contained in the essential oil of the plant. The aromatic volatiles of catnip are produced in the glandular trichomes in the leaf epidermis. Because of the morphological nature of the bilabiate bisexual flowers, this plant can self-pollinate and also has the ability to outcross. Current production methods utilize seeds and transplants from undomesticated populations. While normally cultivated for the pet toy industry as a safe attractant to cats and for ornamental applications, recent research has shown that essential oils from catnip are also an efficient insect repellent and are at least comparable to the industry standard repellent DEET with far less toxicity.

Catnip's volatile oil effectively repels mosquitoes, including the females that carry the *plasmodium* causing malaria and those that transmit yellow fever, filariasis, the West Nile virus, and encephalitis, for a total of six different mosquito species repelled. In one study, 41 different plant species were tested for repellency toward three species of mosquitos that carry pathogens, with *N. cataria* being one of the top five plants whose oil exhibited repellency.

One isomer of nepetalactone, the Z, E isomer, can be hydrogenated to form dihydronepetalactone 2, which is as effective at repelling two species of mosquitoes as DEET and offers complete protection for up to five hours, based on experiments involving human subjects. The Z, E isomer has also shown significant repellency towards house and stable flies, and it has also been reported that catnip-derived nepetalactones are an oviposition repellent. The peach-potato aphid is also repelled by nepetalactones, suggesting that *N. cataria* could be evaluated as an organic pesticide for peach orchards and potato fields. In addition, both the American and German cockroach, which harbor disease causing organisms, were repelled by the nepetalactones present in *Nepeta cataria* and showed better repellency than DEET. Common brown ticks and the deer tick that harbors the bacterium responsible for Lyme disease are repelled by the nepetalactones in *N. cataria* as well as the dihydronepetalactones. Three species of subterranean termites that cause damage to homes and other various wood-based structures resulting in significant financial loss were also repelled by the nepetalactones found in catnip oil. The Z, E nepetalactone isomer was also efficient in repelling many common house dust mite species, as well as poultry mites. In a body contact assay involving harvester ants, mortality was achieved faster with the Z, E nepetalactone isomer than the other nepetalactones in catnip.

Catnip is largely undomesticated, and little breeding has been undertaken to improve the plant's horticultural traits. The present inventors have undertaken genetic collections of catnip (*Nepeta cataria*) and related species sometimes known as catmint (*Nepeta* spp.) including accessions, unimproved lines/populations, and commercial varieties. The purposes of that initial work was to chemically characterize, identify, and develop production systems for commercial farmers and home gardeners to have access to a wide range of catnips that vary in their growth habit or morphology, chemistry, aromatic volatiles, and medicinal applications, including their non-volatile medicinal or bioactivity, and ornamental qualities. In 2004, the inventors began to select and improve catnip for its essential oil yields, growth and production performance and for its essential oil chemistry. Relative to most other members of the Lamiaceae family, catnip is susceptible to diseases and environmental stress, including poor winter survival in northern temperate zones. Tolerant plants can be used as perennials, although they are treated as annuals in commercially grown fields. Commercial fields from transplants are more expensive, as the labor cost is greater and the process is more difficult due to plants dying off and producing less biomass. Further, catnip exhibits a phenotypic architecture that does not lend itself to efficient mechanization. Catnip also produces lower essential oil yields compared to peppermint and spearmint, which have copious amounts of aromatic oils that can be commercially harvested mechanically. The commercialization of catnip as a source for above-ground biomass, essential oils, and isolated Z, E nepetalactone for new insect repellent products remains challenging.

SUMMARY OF THE INVENTION

In one aspect, the invention provides a catnip plant having significantly increased levels of Z, E nepetalactone. In another aspect, the invention provides a plurality of such catnip plants grown in a field. In one embodiment, a plant of the invention is a plant of the catnip cultivar 'CR9', as well as the derivatives of such plants. Further provided by the invention are plant parts, including leaves, cells, plant protoplasts, plant cells of a tissue culture from which catnip plants can be regenerated, plant calli, plant clumps, and plant cells that are intact in plants or parts of plants, such as pollen, flowers, seeds, leaves, stems, roots and the like.

In specific embodiments of the invention, an elevated Z, E nepetalactone level provided by the invention comprises, by percent total essential oils, at least about 87% or more average Z, E nepetalactone content. In other embodiments, a plant of the invention comprising an elevated Z, E nepetalactone level may comprise about 75% to 90%, for example 87% to 90% of Z, E nepetalactone in its chemical profile. In certain embodiments a plant of the invention comprises about 90%, about 89%, about 88%, about 87%, about 86%, about 85%, about 84%, about 83%, about 82%, about 81%, about 80%, or the like. In other embodiments, a plant or part thereof of the invention may comprise a chemical profile as set forth herein, for example as provided in Table 3. For example, such a plant may comprise a chemical profile comprising about 3% 2-pinene, about 87% Z, E nepetalactone, and about 3.5% caryophyllene.

In a further aspect, the invention provides a composition comprising a seed that produces a plant of the invention comprised in plant seed growth media. In certain embodiments, the plant seed growth media is a soil or synthetic cultivation medium. In specific embodiments, the growth medium may be comprised in a container or may, for example, be soil in a field. Plant seed growth media are well known to those of skill in the art and include, but are in no way limited to, soil or synthetic cultivation media. Advantageously, plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

Another aspect of the invention relates to a tissue culture of regenerable cells of a plant of the invention, as well as plants regenerated therefrom, wherein the regenerated catnip plant is capable of expressing all the physiological and morphological characteristics of the plant of the invention.

Yet another aspect of the current invention is a catnip plant comprising a single locus conversion, wherein the catnip plant is otherwise capable of expressing essentially all the physiological and morphological characteristics of the plant of the invention. In particular embodiments of the invention, the single locus conversion may comprise a transgenic gene which has been introduced by genetic transformation. In still other embodiments of the invention, the single locus conversion may comprise a dominant or recessive allele. The locus conversion may confer potentially any trait upon the single locus converted plant, including nutritional value, aromatic value, herbicide resistance, insect resistance, resistance to bacterial, fungal, or viral disease, male fertility or sterility, and improved nutritional quality.

Still yet another aspect of the invention relates to a first generation ($F_1$) hybrid catnip seed produced by crossing a plant of the invention to a second catnip plant. Also included in the invention are the $F_1$ hybrid catnip plants grown from the hybrid seed produced by such crossing. Still further included in the invention are the seeds of an $F_1$ hybrid plant.

Still yet another aspect of the invention is a method of producing catnip seeds comprising crossing a plant of the invention to any second catnip plant, including itself or another plant of the invention. In particular embodiments of the invention, the method of crossing comprises the steps of (a) planting seeds of a plant of the invention; (b) cultivating catnip plants resulting from said seeds until said plants bear flowers; (c) allowing fertilization of the flowers of said plants; and d) harvesting seeds produced from said plants.

Still yet another aspect of the invention is a method of producing hybrid catnip seeds comprising crossing a plant of the invention to a second, distinct catnip plant which is nonisogenic to the plant of the invention. In particular embodiments, the crossing comprises the steps of (a) planting seeds of a plant of the invention and a second, distinct catnip plant, (b) cultivating the catnip plants grown from the seeds until the plants bear flowers; (c) cross-pollinating a flower on one of the two plants with the pollen of the other plant, and (d) harvesting the seeds resulting from the cross pollinating.

Still yet another aspect of the invention is a method for developing a catnip plant in a catnip breeding program comprising: obtaining a catnip plant, or its parts, according to the invention; and employing said plant or parts as a source of breeding material using plant breeding techniques. In the method, the plant breeding techniques may be selected, for example, from the group consisting of recurrent selection, mass selection, bulk selection, backcrossing, pedigree breeding, genetic marker-assisted selection, and genetic transformation. In certain embodiments of the invention, the catnip plant of the invention is used as a male or female parent.

Still yet another aspect of the invention is a method of producing a catnip plant derived from a plant provided herein, the method comprising the steps of: (a) preparing a progeny plant derived from a plant of the invention by crossing the plant with a second catnip plant; and (b) crossing the progeny plant with itself or a second plant to produce a progeny plant of a subsequent generation which is derived from a plant of the invention. In one embodiment of the invention, the method further comprises: (c) crossing the progeny plant of a subsequent generation with itself or a second plant; and (d) repeating steps (b) and (c) for, in some embodiments, at least 2, 3, 4 or more additional generations to produce an inbred catnip plant derived from a plant of the invention. Also provided by the invention is a plant produced by this and the other methods of the invention.

In another embodiment of the invention, the method of producing a catnip plant derived from a plant of the invention further comprises: (a) crossing a derived catnip plant with itself or another catnip plant to yield additional derived progeny catnip seed; (b) growing the progeny catnip seed of step (a) under plant growth conditions to yield additional derived catnip plants; and (c) repeating the crossing and growing steps of (a) and (b) to generate further catnip plants. In specific embodiments, steps (a) and (b) may be repeated at least 1, 2, 3, 4, or 5 or more times as desired. The invention still further provides a catnip plant produced by this and the foregoing methods.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
FIG. 1—Photo of catnip cv. 'CR9' with insect pollinators (just below the arrows).

The invention provides methods and compositions relating to plants, seeds, and derivatives of catnip (*Nepeta cataria*) 'CR9'. Catnip cultivar 'CR9' is the first cultivar of *Nepeta cataria* in North America developed specifically for commercial agricultural production with a more upright growth habit and higher biomass, essential oil, and with a purposefully bred elevated level of Z, E nepetalactone yield (as a function of the relative percentage of the total essential oil yield). In certain embodiments, a plant of the invention comprises elevated levels of Z, E nepetalactone relative to a wild type plant. For example, a plant of the invention may comprise elevated levels of Z, E nepetalactone of about 75% to 90% of total essential oils, for example about 87% to 90% of total essential oils in its chemical profile. In certain embodiments, a plant provided by the invention may exhibit a total Z, E nepetalactone yield of 1 g per plant, for example a total Z, E nepetalactone yield of 1.5 g per plant, 1.6 g per plant, or 1.7 g per plant, or a 50%, 60%, 70%, 75%, or 77% improvement in total Z, E nepetalactone yield over a wild type plant or the closest commercial line in a growing season. Essential oil from currently cultivated varieties contains many aromatic volatile compounds, including nepetalactone. Catnip cultivar 'CR9' was developed and is distinct from all other commercially available sources because it produces a uniform seeded offspring with the desired characteristics and with a novel chemistry relative to the concentration of Z, E nepetalactone. The selfed progeny of 'CR9' produce higher amounts of biomass, essential oil yields, and the essential oil is richer in the bioactive isomer Z, E nepetalactone in these populations and amounts are significantly higher than anything previously reported. 'CR9' provides a superior catnip plant for commercial field production, for dried catnip, or for the distilled aromatic essential oils that have multiple applications, including the pet toy and insect repellent industries.

A. Origin and Breeding History of Catnip Hybrid 'CR9'

'CR9' was developed after six different randomized complete block growth trials by selecting the best field performing plants that grew the most upright, survived the winters in New Jersey, and produced the highest above-ground biomass and essential oil and Z, E nepetalactone yields. In 2001, the USDA *N. cataria* germplasm was comparatively grown at the Rutgers Clifford E. & Melda Snyder Research Farm, in Pittstown, N.J. along with a wide range of commercial catnip varieties in a seeded field trial. For two growing seasons, individual plants that were off-types and exhibited poor performance and/or winter injury were removed from the study. In 2002, the remaining plants from the best performing USDA line PI# W6 17691 were allowed to outcross by wind and bees, the seed was collected from the remaining individual plants, and the new advanced breeding line was formed. In 2005, these seeds were sown in a field trial at the Rutgers Fruit and Ornamental Research Extension Center in Cream Ridge N.J., to identify lines with the desired phenotypic characteristics and to evaluate their uniformity. Only the most promising plants were left in the field, all others were removed. In 2006, after the plants were subjected to the winter season and assessed for winter survival, selections were made from this field with respect to biomass and winter survival by taking cuttings of the individual plants and allowing them to self-pollinate in a research greenhouse. In 2007, those selfed seeds were planted in another two-year evaluation at the Rutgers Clifford E. & Melda Snyder Research Farm, in Pittstown, N.J. Selections took place in the second year after the plants were subjected to the winter season. Plant selections were also largely based upon total essential oil production (e.g., yield/plant) and Z, E nepetalactone concentration. The selections from 2008 were then clonally evaluated for two additional years in 2010 and 2011 at the same research farm to ensure minimal environmental influence on the variation of essential oil yields and nepetalactone concentration. Those clones were then selfed and the seed was used in the next growth trial in 2013. The genealogy of cultivar 'CR9' is provided in Table 1.

Table 1: Genealogy of the New Catnip Cultivar 'CR9' (*Nepeta cataria*)

2001 Original seeded field establishment for catnip evaluation of the USDA germplasm and commercial lines including USDA germplasm PI # W6 17691.
  Evaluation for desired morphological characteristics and the rouging out of poor performing plants was performed.
2002 Plants remaining in 2002 that successfully overwintered from 2001 and exhibited desired morphological characteristics formed the breeding lines (C244, C245, C246, C47, C248, C249, and G1) and were allowed to outcross.
2005 The outcrossed seeds from lines (C244, C245, C246, C47, C248, C249, and G1) were sown in a field trial and evaluated for desired phenotypic characteristics as well as the rouging out of poor performing plants.
2006 Plants remaining from the 2005 field trials and which exhibited desired phenotypic characteristics were selected forming the breeding line (CR).
  CR breeding lines were allowed to self-pollinate in a research greenhouse.
2007 The CR line was sown in a field growth trial in which individual plants were identified for desired phenotypic characteristics with emphasis on essential oils.
2008 Selections of advanced lines including CR9 from the CR breeding lines were made after the 2007 winter with emphasis on essential oil characteristics, winter hardiness, growth habit, and biomass and essential oil yields and chemical profiles.
2010 Clonal evaluation of CR9 in comparison to other advanced catnip lines for desired morphological characteristics and essential oil analysis was conducted.
2011 Clonal evaluation of seven advanced breeding lines including CR9 for desired morphological characteristics and essential oil analysis was conducted.
  Breeding lines were allowed to self-pollinate in a research greenhouse.
2013 Final seeded evaluation of the selfed, advanced breeding line 'CR9' the five and commercial lines for comparison and to ensure stability of the self-seeded progeny of CR9.

Selection of 'CR9' for the new catnip cultivar *Nepeta cataria* L. 'CR9'

In 2013, the clones demonstrating uniform production of essential oil yields and nepetalactone concentration had their selfed progeny planted in a final seeded field evaluation that year at the New Jersey Agricultural Experiment Station Clifford E. & Melda Snyder Research Farm, in Pittstown, N.J. The progeny of 'CR9' was field grown and compared to commercial seed companies offering catnip (Johnny's Selected Seeds, Albion, Me.; Ferry Morse, Norton, Mass.; Stokes, Buffalo, N.Y.; Territorial Seed Company, Cottage Grove, Oreg.; Richters Herbs, Goodwood, Ontario, Canada). The land was cultivated by disc plowing and raised beds were then mechanically prepared, followed by the placement of drip irrigation and plastic mulch. The land was fertilized at 900 lbs/acre of 15-15-15 and was irrigated through drip irrigation as needed and as described (Park et al., 2007). The experimental design for 2013 was a randomized complete block design with 10 plants in each of the six lines having their morphological characteristics recorded for each of the three replications. The plants were spaced 61 cm apart within the rows and the rows were spaced 274 cm apart. Once the plants were in full flower, morphological characteristics were recorded, the plants were cut back to the ground level after 10 weeks, and the entire plot was bulk harvested and dried on site at 37° C. using a walk-in forced-air commercial Powell Tobacco dryer converted to the drying of herbs and botanicals. Plant height, plant width, leaf length, leaf width, and dry weights were recorded. Plant height was measured from the soil level to the flowers down the center of the plant. Plant width was determined by measuring the diameter of the plant. Leaf length was the measurement from the tip of the leaf to the beginning of the petiole on the side that connects to the leaf. The width of the leaf was measured at the basal portion of the leaf at the largest diameter. Dry weights were determined by recording the weight after plants had lost all the water at the set unified temperature of 37° C. The plants in the field were allowed to grow again to maturity, at which point they were again bulk harvested as described above and dried on site at 37° C. Essential oil yields were determined by the hydro distillation of all of the above-ground biomass of the plant using a Clevenger-type distillation unit with 100 g of dry plant matter. The yields were calculated as percent of dry mass (mg essential oil/100 g above-ground biomass). Essential oil analysis was performed by quantitatively comparing the samples using a flame ionization detector and qualitatively by identifying the chemical constituents of the oil with mass spectrometry (Juliani et al., 2008).

B. Physiological and Morphological Characteristics of Catnip Hybrid 'CR9'

The new catnip cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Color Chart of The Royal Horticultural Society, London, England, 2015 edition, except where general color terms of ordinary significance are used. The color values were determined in July of 2016 under natural light conditions in West Chicago, Ill.

The following descriptions and measurements describe approximately 16-month-old plants produced from cuttings. The plants were grown utilizing a soilless growth medium, and were then transplanted to a field in Capay, Calif. in July of 2015. Plants were not pinched, however flowers were removed in the fall of 2015. Measurements and numerical values represent averages of typical plants.

The physiological and morphological characteristics of catnip cultivar 'CR9' are as follows:

Plant Description:
  Growth habit and general appearance—Herbaceous perennial, upright mounding with side stems becoming decumbent.
  Size—Height from soil level to top of plant plane: About 50.0 cm. Width: About 65.0 cm.
  Branching habit—Freely branching. Quantity of branches per plant: About 36 main basal branches.
  Branch—Shape: Square in cross section. Strength: Strong. Length to base of inflorescence: About 39.0 cm. Diameter: About 3.0 mm. Length of central internode: About 5.5 cm. Texture: Densely pubescent with soft, short hairs. Color of young stems: 146D. Color of mature stems: 146B.
  Root—Fine, freely branching, spreads through rhizomes.
Foliage Description:
  General Description—Quantity of leaves per main branch: About 12. Fragrance: Strong, minty. Form: Simple. Arrangement: Opposite.
  Leaves—Aspect: Acute to perpendicular angle to stem. Shape: Ovate. Margin: Crenate. Apex: Acute. Base: Cordate. Venation pattern: Longitudinally grooved, impressed on adaxial surface and ribbed on abaxial surface. Length of mature leaf: About 3.0 cm. Width of mature leaf: About 2.8 cm. Texture of upper and lower surfaces: Densely pubescent. Color of upper surface of young and mature foliage: 137B with venation of 137A. Color of lower surface of young and mature foliage: Closest to but greener than N138C, venation of 145C.
  Petiole—Length: About 1.0 cm. Diameter: About 1.0 mm. Texture: Densely pubescent with soft, short hairs. Color: 145B.
Inflorescence Description:
  General description—Type: Terminal and lateral cymosely clustered with flowers either sessile or branched in verticillaster arrangement in the upper nodes, florets in clusters of 8 to 12, not persistent. Quantity of inflorescences per plant: About 36. Fragrance: Strong, minty. Length or height of terminal inflorescences: About 6.0 cm. Width of terminal inflorescences: About 3.0 cm. Length or height of lateral inflorescences: About 2.0 cm. Width of lateral inflorescences: About 1.0 cm.
  Peduncle—Shape: Square in cross section. Strength: Strong. Aspect: Erect. Length for terminal cluster: About 2.0 cm. Diameter: About 2.0 mm. Texture: Densely glandular pubescent. Color: 146D.
Flower Description:
  Type—Single, zygomorphic.
  Bud—Rate of opening: Generally takes 2 to 3 days for bud to progress from first color to fully open flower.
  Bud just before opening—Shape: Obovoid. Length: About 5.0 cm. Diameter: About 2.0 mm. Texture: Densely pubescent. Color: Calyx portion of 138B and petal portion of NN155B.
  Corolla—Shape: Bilabiate, upper lip two lobes and lower lip having three lobes, base fused. Width: About 4.0 mm. Length: About 5.0 mm. Depth: About 7.0 mm.
  Upper lip—Shape: Obovate, highly reflexed. Margin: Entire. Apex: Rounded. Length from throat: About 2.0 mm. Width: About 1.0 mm. Texture of inner surface: Glabrous. Texture of outer surface: Sparsely pubescent. Color of inner surface when first and fully open: NN155D. Color of outer surface when first and fully open: NN155D.
  Lower lip—Shape of lateral lobes: Oblong. Shape of central lobes: Obovate. Margin: Entire. Apex of central lobe: Scalloped. Apex of lateral lobes: Rounded. Length from throat of central lobe: About 3.0 mm. Width of central lobe: About 4.0 mm. Length from throat of lateral lobes: About 0.5 mm. Width of lateral lobes: About 1.0 mm. Texture of upper surface of lateral lobes: Glabrous. Texture of upper surface of central lobe: Densely pubescent at throat opening. Texture of lower surface of lateral and central lobes: Sparsely pubescent. Color of upper surface when first and fully open: NN155D. Color of lower surface when first and fully open: NN155D.
  Corolla tube—Length: About 5.0 mm. Diameter at opening: About 2.0 mm. Diameter at base: About 1.0 mm. Texture of inner surface: Glabrous. Texture of outer surface: Densely pubescent. Color of inner surface when first and fully open: NN155D. Color of outer surface when first and fully open: NN155D.
  Calyx—Shape: Tubular. Length: About 5.0 mm. Diameter: About 1.5 mm.

Sepals—Quantity per flower: 5. Shape: Linear. Apex: Acute. Length: About 5.0 mm. Width of lobes: About 1.0 mm. Texture of inner surface: Moderately pubescent. Texture of outer surface: Densely pubescent. Color of inner surface: 138C. Color of outer surface: 138B.

Pedicel—Strength: Strong, flexible. Length: About 1.0 mm. Diameter: About 0.5 mm. Texture: Densely pubescent. Color: 146D.

Reproductive organs—Androecium: Stamen quantity: 4 per flower, adnate to corolla tube. Stamen length: About 4.0 mm. Filament length of free portion: About 0.5 mm. Filament color: NN155D. Anther shape: Bi-lobed. Anther length: About 0.5 mm. Anther color: NN155B. Pollen amount: Moderate. Pollen color: NN155D. Gynoecium: Pistil quantity: 1 per flower, slightly curved. Pistil length: About 7.0 mm. Stigma shape: Cleft, two-parted. Stigma length: Less than 1.0 mm. Stigma color: NN155D. Style length: About 6.0 mm. Style color: NN155D. Ovary length: About 1.0 mm. Ovary color: N144D.

Figure 2:
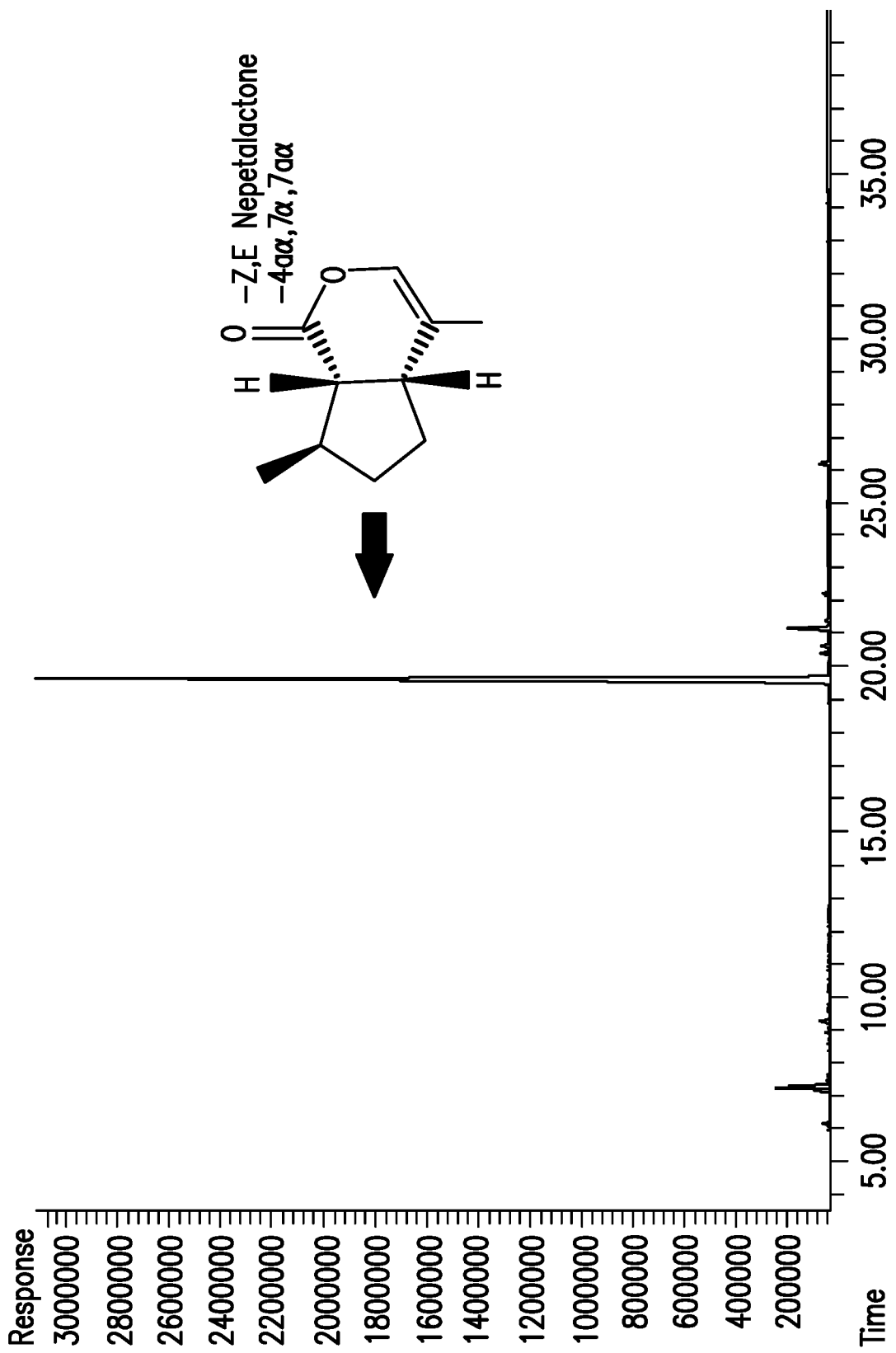
FIG. 2—Gas chromatogram of the essential oil also referred to as the aromatic volatile oil, from catnip cultivar 'CR9' illustrating the peak of Z, E nepetalactone.
Figure 3:
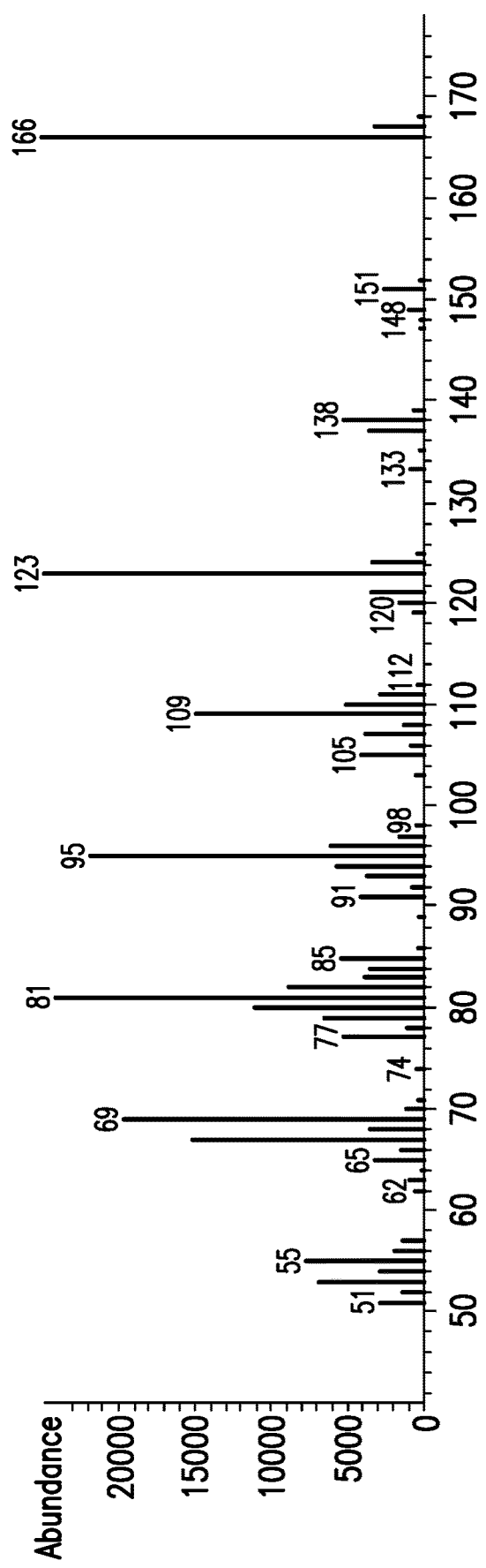
FIG. 3—Mass spectra of Z, E nepetalactone, the major compound found in the essential oil of catnip 'CR9'.

As described above, the progeny of the 'CR9' cultivar of N. cataria have opposite triangular ovate leaves that have crenate edges. All of the leaves are dark to light green. These plants are bushy and flower within 90 days. The white bilabiate flowers are grown on terminal inflorescences in whorls. 'CR9' plants were the tallest and had the largest leaves. Once cut back and allowed to regrow, 'CR9' plants remained the tallest but the leaf dimensions resemble the commercial lines in the same study (Table 2). In central New Jersey's growing zone six (40.559340, −74.961282), this plant can be harvested twice in a growing season for biomass, essential oils, and for Z, E nepetalactone. Catnip cultivar 'CR9' can also be kept from flowering by continual pruning. The plants serve as an excellent source for pollinators. Bees, butterflies, and many other insects frequently visited all the catnips, including the progeny of 'CR9' plants during the entire flowering period (FIG. 1). Chemical characterization of the essential oil of these plants using both gas chromatography (GC) and mass spectroscopy (MS) with alkane standards confirmed the presence of Z, E nepetalactone (FIGS. 2 and 3) (Adams, 2007).

Performance

'CR9' performed far better than selections from each of the commercial seed companies to which it was compared. 'CR9' has a mean dry weight per plant of 158.0 g per plant on the first harvest and 177.0 g on the second harvest for a total of 335 g per year with a 33% improvement over the closest commercial line. Plants of the invention produce about 0.8% essential oil as a percent of dry weight. The essential oil yield per plant is 1.54 g per plant on the first harvest and 1.38 g per plant on the second harvest, for a total of 2.92 g per year with a 54% improvement over the closest commercial line. Z, E nepetalactone yield was 1.34 g per plant on the first harvest and 0.35 g on the second harvest for a total of 1.7 g per year with a 77% improvement over the closest commercial line. The concentration of Z, E nepetalactone was 87% on the first harvest, and 25% on the second harvest, with all catnip lines evaluated exhibiting decreased concentration of Z, E nepetalactone. The chemical profile of catnip variety 'CR9' is provided in Table 3. 'CR9' survived winter conditions and exhibited the least winter injury and die-back compared to the commercial catnips that were evaluated. As a garden herb, 'CR9' s progeny can live for many additional years on the landscape and could be considered aesthetically attractive with light-green, soft leaves and a highly pleasant spice-like aroma. This new cultivar lends itself more to mechanical harvesting as is required for larger-scale essential oil production and was developed for this purpose. Because of the increased essential oil, commercialization of this catnip cultivar as an essential oil crop is more realistic than prior and currently available catnip lines. 'CR9' could result in significantly increased revenue for those involved in using the essential oil of catnip from the cat and toy industry, to those interested in the use of the oil and/or dry leave as an herbal infusion and tea for health and nutrition purposes and for the insect repellent industry significantly, given that the cultivar was developed as an improved source of essential oil for growers with steam distillation facilities and/or with drying and processing facilities.

TABLE 2

Morphological and essential oil characteristics of the new catnip cultivar 'CR9' compared to commercial catnip varieties over two harvests, 2013$^z$.

|  | Morphological Characteristics | | | | | Essential Oil Analysis | |
| --- | --- | --- | --- | --- | --- | --- | --- |
|  | | | | | | | Z, E |
| 2013 First Harvest | Plant Height (cm) | Plant Spread (cm) | Leaf Length (cm) | Leaf Width (cm) | Dry Weight Per Plant (g) | Oil Yield (g) Per Plant | Nepetalactone Yield (g) per Plant |
| CR9 | 65.9 A$^y$ | 92.1 BC | 6.0 A | 4.8 A | 158.0 A | 1.54 A | 1.34 A |
| JON | 56.5 B | 98.0 AB | 4.7 B | 3.5 B | 115.0 B | 1.05 B | 0.74 B |
| RICH | 55.4 B | 100.9 A | 4.8 B | 3.6 B | 113.3 B | 0.90 B | 0.73 B |
| STOKE | 53.3 B | 94.0 AB | 4.9 B | 3.7 B | 127.7 B | 1.21 AB | 0.22 C |
| TERR | 55.9 B | 101.3 A | 4.4 B | 3.3 B | 112.3 B | 1.16 AB | 0.21 C |
| CFM | 50.4 C | 87.5 C | 4.0 C | 3.4 B | 88.0 C | 0.46 C | 0.06 C |

|  | Morphological Characteristics | | | | | Essential Oil Analysis | |
| --- | --- | --- | --- | --- | --- | --- | --- |
|  | | | | | | | Z, E |
| 2013 Second Harvest | Plant Height (cm) | Plant Spread (cm) | Leaf Length (cm) | Leaf Width (cm) | Dry Weight Per Plant (g) | Oil Yield (g) Per Plant | Nepetalactone Yield (g) per Plant |
| CR9 | 51.1 A | 82.5 AB | 5.8 A | 4.1 A | 177.0 A | 1.38 A | 0.35 A |
| CFM | 46.3 B | 89.7 A | 5.7 A | 3.7 A | 136.0 A | 0.84 B | 0.21 B |

TABLE 2-continued

Morphological and essential oil characteristics of the new catnip cultivar 'CR9' compared to commercial catnip varieties over two harvests, 2013[z].

| STOKE | 43.3 | B | 80.7 | AB | 5.7 | A | 3.7 | A | 115.7 | A | 0.73 | BC | 0.19 | B |
| RICH | 44.3 | B | 83.1 | AB | 5.5 | A | 3.7 | A | 157.3 | A | 0.63 | BC | 0.16 | B |
| TERR | 43.3 | B | 77.5 | B | 6.0 | A | 3.9 | A | 101.7 | B | 0.50 | BC | 0.13 | B |
| JON | 39.4 | C | 79.7 | AB | 5.8 | A | 3.9 | A | 125.0 | A | 0.42 | C | 0.11 | C |

[z]CR9 = Rutgers new cultivar release;
CFM = Ferry Morse Seeds, Norton, MA;
JON = Johnny's Selected Seeds, Albion, ME;
RICH = Richters Herbs, Goodwood, Ontario, Canada;
STOKES = Stokes Seeds, Buffalo, NY;
TERR = Territorial Seed Company, Cottage Grove, OR;)
[y]Value within columns followed by the different letters are significantly different according to Duncan's test at $P \leq 0.05$.

TABLE 3

Chemical profile of the new catnip cultivar 'CR9'

| % | Compound Name |
|---|---|
| 3% | 2-pinene |
| 87% | Z,E Nepetalactone |
| 3.50% | Carophyllene |
| 93.5% | Total |

Insect Repellancy

Figure 4:
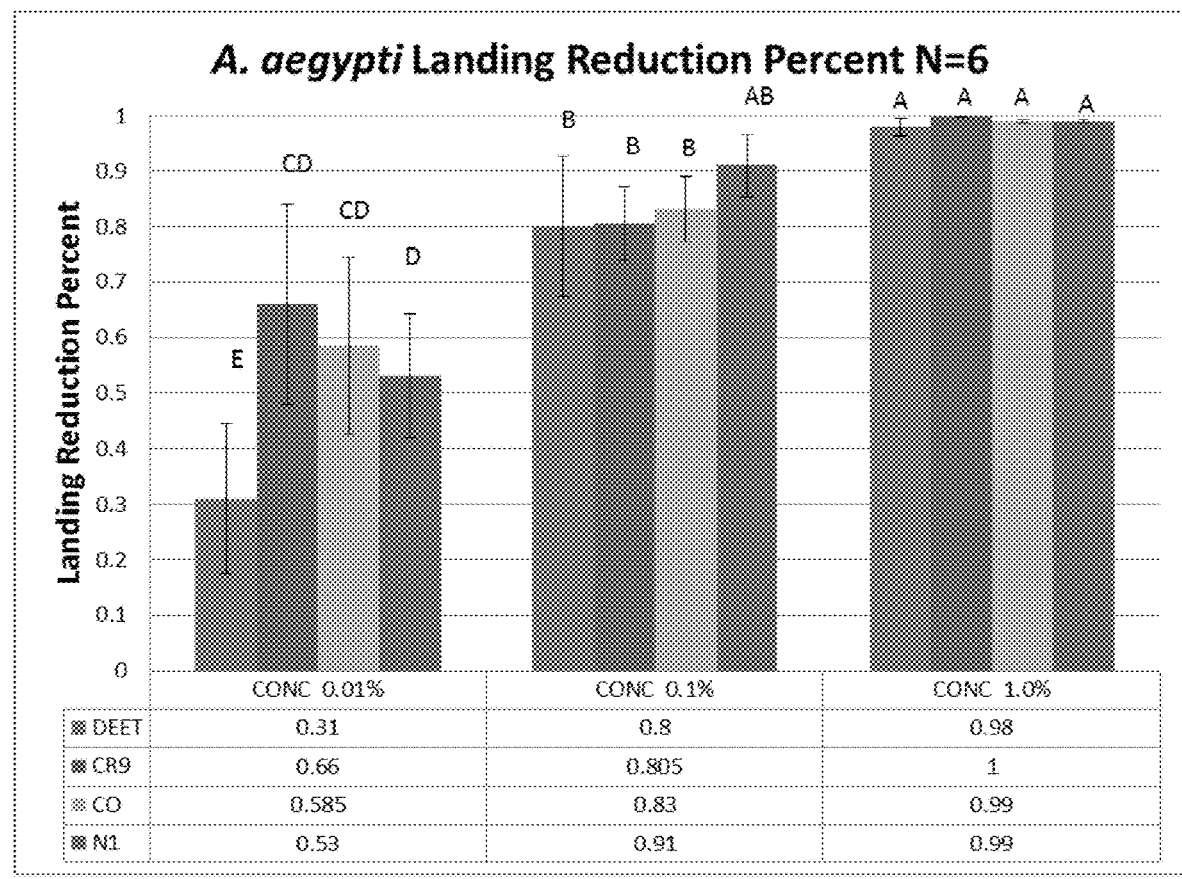
FIG. 4—Dose dependent landing inhibition curve for A. aegypti following various repellent treatments at 0.01%, 0.10% and 1.00%. Values within columns followed by the different letters are significantly different according to Duncan's test at $P \leq 0.05$.
Figure 5:
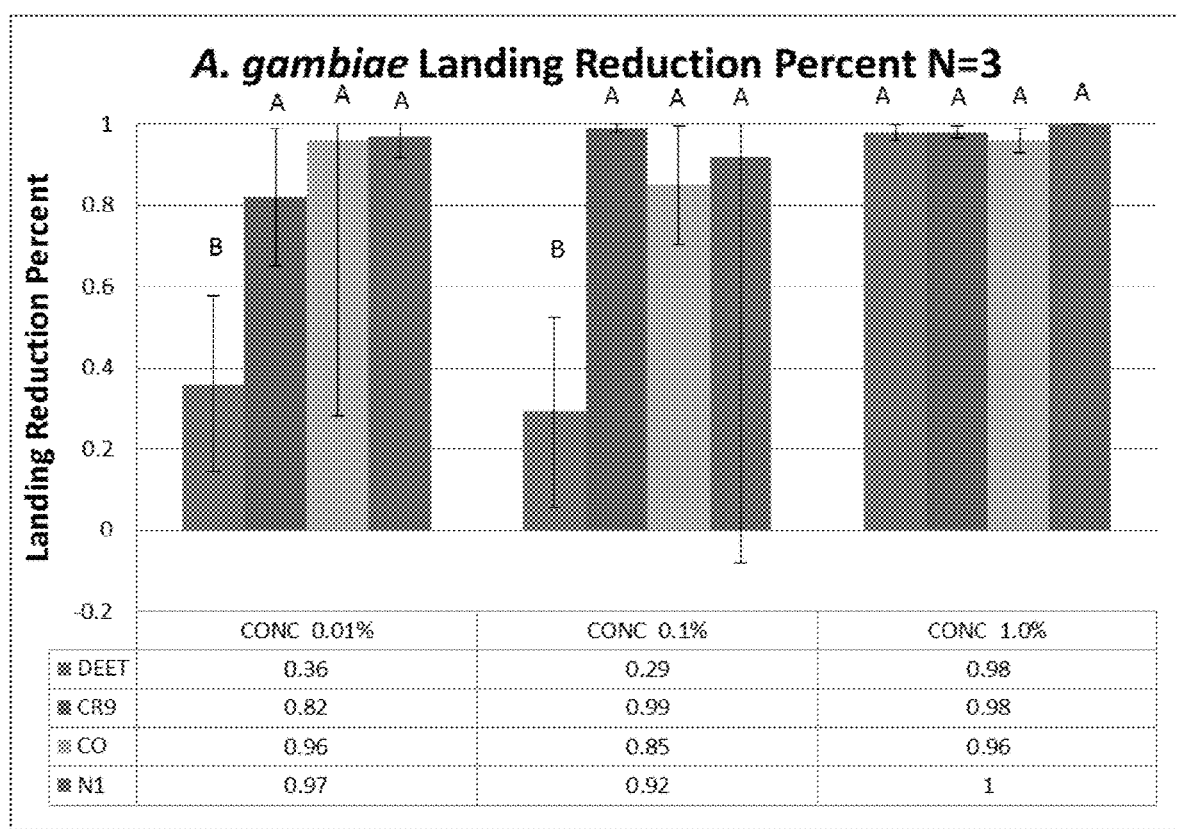
FIG. 5—Dose dependent landing inhibition curve for A. gambiae following various repellent treatments at 0.01%, 0.10% and 1.00%.

Essential oils prepared from 'CR9' plants also exhibited insect repellant properties when tested in a mosquito landing rate inhibition assay against DEET. Nepeta cataria plants were evaluated as insect repellents against Aedes aegypti and Anopholes gambiae mosquitoes in a landing rate inhibition assay against DEET as shown in FIGS. 4 and 5. A dose dependent curve was generated for all treatments and a time course analysis was performed with a crude essential oil sample. The results indicate that all tested crude essential oil samples and their respective purified nepetalactone isomers were able to achieve greater than 95% repellency. Between two and four hours the ability to generate 95% repellency diminished. At the lowest concentration tested, the nepetalactones and crude essential oil samples were more effective than DEET at reducing the number of mosquito landings.

Nepeta cataria Cultivation and Essential Oil Preparation

The clonal population serving as source material for the essential oils were the 'CR9' cultivar. The hydro-distilled essential oil from these two populations was used as the source for the crude essential oil treatments and was partitioned for subsequent fractionation and nepetalactone purification.

Vegetative clones of the two populations were made by making cuttings at the terminal nodes and briefly dipping them in Hormodin 2® 0.3% indole-3-butyric acid (IBA) to induce root formation and placed them in a mister until roots developed. The clones were then transplanted to the field. Immediately before the plants were in full flower, they were harvested and dried at 37° C. with an onsite Powell walk-in forced air heat dryer. Once the plants had lost all moisture, the leaves and flowers were separated from the stems for hydro-distillation. Essential oils were extracted by hydro-distilling 60 g of dried N. cataria leaves and flowers. They were distilled in a 2 L round bottom flask for 3 hours in 1 L of water and the essential oil was collected in a Clevenger-type trap. The essential oils were then prepared and analyzed by GC/MS. The CR9 essential oil contained 90.1% Z, E nepetalactone and less than 0.5% E, Z nepetalactone (% of the total essential oil).

GC/MS Sample Preparation and Injection Conditions

Essential oil samples were prepared by the extraction 10 µL of crude N. cataria essential oil with 1.5 ml of TMBE which was then dried over anhydrous sodium sulfate and centrifuged at 13Krpm. The supernatant was transferred to a sampling vial for analysis. Essential oil separation was done on a Shimadzu 2010 Plus gas chromatograph equipped with and AOC-6000 auto-sampler and the calculation of the relative abundance of compound fragments was performed on a Shimadzu TQ8040 MS.

The injection volume of 1 µL was separated on a H-Rxi-5Sil MS column heated from 35° C. with a hold of 4 min to 250° C. with a hold of 1.25 min at 20° C./min. The inlet temperature was 250° C. with a split less injection. The ion source temperature was set to 200° C., the interface temperature was set to 250° C., the solvent cut time was 3.5 min, and the detector voltage was set to 0.2 kV with a threshold of 1000. Peak integration percentages were calculated using the GCMS solution v4.3© software from Shimadzu Corporation. Individual compound identities were determined by comparing the mass spectral results to current literature and screening them in the NIST05.LIB, NIST05s.LIB, W10N14.lib and the W10N14R.lib mass spectral libraries.

Mosquito Rearing

Mosquito eggs were reared in water at 27° C. with 80% humidity and the mosquitoes were transferred during the rearing process with an eye dropper. The A. aegypti eggs were placed in a container holding water and once hatched and formed into larvae, they were separated from the unhatched eggs and placed into fresh water. General fish food tablets were used as the energy source for the maturing mosquitoes. As the mosquitoes began to form into pupae, they were separated from the smaller less developed larvae and placed into fresh water. This container was then placed into a Bug Dorm Cage where the pupae were allowed to mature into adults. Mature females were then separated out of this population of mature adults by aspirating them into a separate container Bug Dorm Cage where they were given a 10% sucrose solution as an energy source. Mature females were kept at these conditions until they were used for experimentation.

Dose Dependent Curve Generation

Repellency was determined by a one-choice landing assay that uses the amount of mosquito landings to calculate the overall effectiveness of the candidate repellent. Twenty, one day starved adult female Aedes aegypti mosquitoes were aspirated into a Bug Dorm Cage. Testing was performed between 10:00 am and 4:00 pm PST during A. aegypti's host seeking hours. A HotHands® heat pack was used as the heat source to attract the mosquitoes in the upper region of the back panel. Treatments were applied to a Whatman® filter paper and used to wrap the heat source. A control of just acetone was applied to the filter papers before and after each treatment to ensure reproducibility in mosquito behavior. The curve was generated from identifying a concentration of the treatments that exhibited complete repellency and then working in reverse logarithmically. Initial tests showed that few enough landings were observed at 1.0% generating a greater than 95% reduction in mosquito landings and was defined as complete repellency. Time lapse photography recorded one image every five seconds. A custom was used to count the mosquitoes automatically through the open source image processing software ImageJ.

Time Course Assay

Repellency was determined by a one-choice assay that uses the total amount of mosquito landings to judge the overall effectiveness of the repellent. The assay is performed the same way as the dose dependent curve, except the Whatman filter papers were saved and evaluated over a 24 hr period at the 0 hr, 1 hr, 2 hr, 4 hr, 8 hr and 24 hr intervals.

Results

In the dose dependent curve, DEET and all of the catnip treatments at 1.00% decreased the landings of mosquitoes by >95% and all of the 1.00% treatments grouped together statistically in repellency (FIGS. 4 and 5). At 0.10%, Z, E nepetalactone generated the highest repellency percentage. The rest of the treatments were not significantly different from one another at 0.10%. At the lowest concentration, all of the catnip extracts were significantly higher than DEET at reducing landings.

Figure 6:
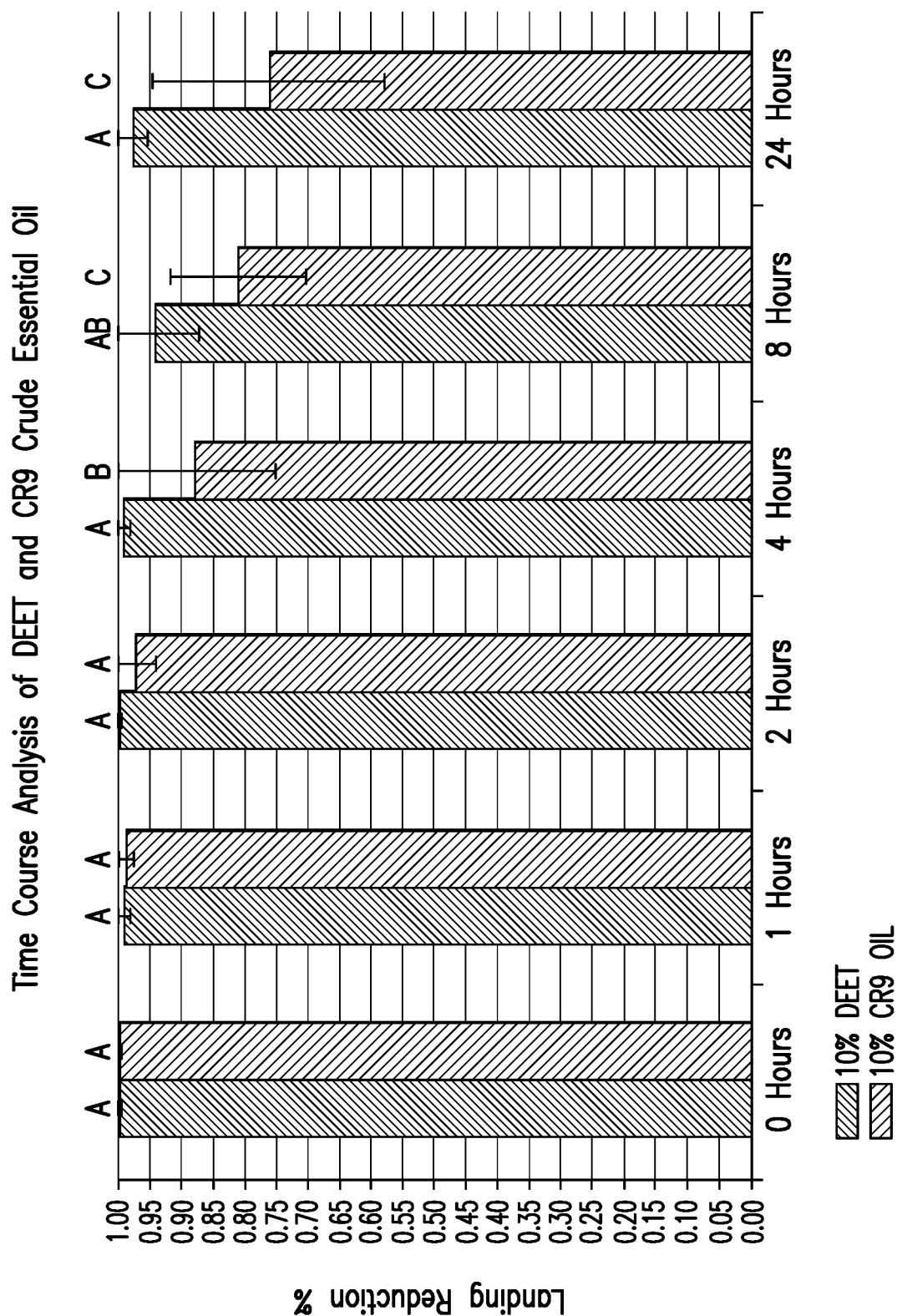
FIG. 6—Time course analysis comparing 10% DEET and crude CR9 essential oil over 24 hours. Values within columns followed by the different letters are significantly different according to Duncan's test at $P \leq 0.05$.

In the time course assay, the 10.00% CR9 essential oil treatment generated >95% repellency for the first two hours and was statistically similar to DEET. In-between 2 and 4 hours, this repellency diminished and did not meet the >95% level and it was no longer statistically similar to DEET (FIG. 6). After 24 hours, the essential oil present on the filter paper was able to generate a repellent effect. The DEET treatment was able to maintain the >95% repellency rate throughout the 24 hr period.

C. Breeding Catnip Plants

One aspect of the current invention concerns methods for producing seed of catnip hybrid 'CR9'. Alternatively, in other embodiments of the invention, hybrid 'CR9' may be crossed with itself or with any second plant. Such methods can be used for propagation of hybrid 'CR9' or can be used to produce plants that are derived from hybrid 'CR9'. Plants derived from hybrid 'CR9' may be used, in certain embodiments, for the development of new catnip varieties.

The development of new varieties using one or more starting varieties is well known in the art. In accordance with the invention, novel varieties may be created by crossing hybrid 'CR9' followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Backcrossing can be used to improve a variety, and may be used, for example, to introduce a desired allele or trait into the plant genetic background of any plant that is sexually compatible with a plant of the present invention. Backcrossing transfers a specific desired trait from one inbred or non-inbred source to a variety that lacks that trait. This can be accomplished, for example, by first crossing a variety of a desired genetic background (recurrent parent) to a donor inbred (non-recurrent parent), which carries the appropriate allele or loci for the desired trait(s) in question. The progeny of this cross are then mated back to the recurrent parent, followed by selection in the resultant progeny for the desired trait to be transferred from the non-recurrent parent. The process is repeated, for example for five or more backcross generations with selection for the desired trait, until a plant is obtained wherein essentially all of the desired morphological and physiological characteristics of the recurrent parent are recovered in the converted plant, in addition to the single transferred locus from the nonrecurrent parent. The progeny thus have the characteristic being transferred, but are like the superior parent for most or almost all other loci. The last backcross generation can be selfed to give true-breeding progeny when the trait being transferred is introgressed into a true-breeding variety.

The recurrent parent therefore provides the desired genetic background, while the choice of the particular non-recurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred.

Modified backcrossing may also be used with plants of the present invention. This technique uses different recurrent parents during the backcrossing. Modified backcrossing may be used to replace the original recurrent parent with a variety having certain more desirable characteristics or multiple parents may be used to obtain different desirable characteristics from each.

The plants of the present invention are particularly well suited for the development of new lines based on the genetic background of the plants. In selecting a second plant to cross with 'CR9' for the purpose of developing novel catnip lines, it will typically be preferred to choose those plants which either themselves exhibit one or more selected desirable characteristics or which exhibit the desired characteristic(s) when in hybrid combination. Examples of desirable traits may include, in specific embodiments, high flower yield, flower quality, high seed germination, seedling vigor, disease resistance, and adaptability for soil and climate conditions such as drought or heat. Consumer-driven traits, such as flower color, shape, and texture, even aroma and taste are other examples of traits that may be incorporated into new lines of catnip plants developed by this invention.

D. Further Embodiments of the Invention

In other embodiments, the invention provides methods of vegetatively propagating a plant of the present invention. Such a method may comprise the steps of: (a) collecting tissue capable of being propagated from said plant; (b) cultivating said tissue to obtain proliferated shoots; and (c) rooting said proliferated shoots to obtain rooted plantlets. In other embodiments, such a method may further comprise growing catnip plants from the rooted plantlets. In still further embodiments, a plant of the invention is propagated by seed, wherein a plant may be used as either a female or a male parent for producing progeny seed and plants.

Also provided are methods of producing a catnip plant of the present invention, said method comprising introgressing a desired allele from a plant comprising the allele into a plant of a different genotype. In certain embodiments, such an allele may be inherited from or introgressed into catnip hybrid 'CR9' or a progeny of any generation thereof comprising the allele.

Many single locus traits have been identified that are not regularly selected for in the development of a new inbred but that can be improved by backcrossing techniques. Single locus traits may or may not be transgenic; examples of these traits include, but are not limited to, resistance to bacterial, fungal, or viral disease, or herbicide or insect resistance. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of catnip plants for breeding is not necessarily dependent on the phenotype of a plant and instead can be based on genetic investigations. Thus, in one embodiment, the invention provides the genetic complement of a catnip plant as described herein. "Genetic complement" as used herein refers to the aggregate of nucleotide sequences, the expression of which sequences defines the phenotype of, in the present case, a catnip plant, or a cell or tissue of that plant. A genetic complement thus represents the genetic makeup of a cell, tissue or plant, and a hybrid genetic complement represents the genetic make up of a hybrid cell, tissue or plant. The genetic complement of variety 'CR9' may be identified by any of the many well-known techniques in the art. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker-assisted selection.

Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiology*, 147: 969-977), for example, and elsewhere, provides a mechanism for integrating single or multiple traits or QTL into a line. This molecular breeding-facilitated movement of a trait or traits into a line or variety may encompass incorporation of a particular genomic fragment associated with a particular trait of interest into the line or variety by the mechanism of identification of the integrated genomic fragment with the use of flanking or associated marker assays. In the embodiment represented here, one, two, three or four genomic loci, for example, may be integrated into a line via this methodology. When this line containing the additional loci is further crossed with another parental line to produce hybrid offspring, it is possible to then incorporate at least eight separate additional loci into the hybrid. These additional loci may confer, for example, such traits as disease resistance, drought or heat tolerance, or a flower quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

E. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107: 462-469, 2003).

A number of promoters have utility for plant gene expression for any gene of interest including but not limited to selectable markers, scoreable markers, genes for pest tolerance, disease resistance, or any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S); 1 the nopaline synthase promoter (An et al., *Plant Physiol.*, 88:547, 1988); the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a *commelina* yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a catnip plant according to the invention. Non-limiting examples of particular genes and corresponding phenotypes one may choose to introduce into a catnip plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

F. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid (F1), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

F1 Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Plant Part: As used herein, a plant part refers to a part of a plant of the present invention. A plant part may be defined as comprising a cell of such plant, such as a cutting, a leaf, an ovule, pollen, a cell, a seed, a flower, an embryo, a meristem, a cotyledon, an anther, a root, a root tip, a pistil, a stem, and a protoplast or callus derived therefrom.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a catnip cultivar are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a catnip plant by transformation.

Catnip plant: As used herein, catnip refers to any plant from the genus *Nepeta*, which may include but is not limited to *Nepeta cataria*. As used herein, catnip may also refer to a variant, progeny, or offspring of such a plant, including a plant or part thereof. The terms variety, cultivar, or the like may be used interchangeably to refer to a plant of the present invention.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

G. Deposit Information

A deposit of catnip cultivar 'CR9', disclosed above and recited in the claims, has been made with the American Type Culture Collection (ATCC), 10801 University Blvd., Manassas, Va. 20110-2209. The date of the deposit was Sep. 13, 2019. The accession numbers for those deposited seeds of catnip cultivar 'CR9' are ATCC Accession Number PTA-126211. Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A plant of catnip cultivarl 'CR9', wherein a representative sample of seed of catnip cultivar 'CR9' has been deposited under ATCC Accession No. PTA-126211.

2. A plurality of plants according to claim 1 grown in a field.

3. A plant part of the plant of claim 1, wherein the plant part comprises at least one cell of said plant.

4. The plant part of claim 3, further defined as a leaf, pollen, a meristem, a cell, a seed, or an ovule.

5. A seed that produces the plant of claim 1.

6. The plant of claim 1, wherein the essential oil profile comprises about 87% or about 90.1% Z, E nepetalactone.

7. A method of producing catnip seed, the method comprising crossing the plant of claim 1 with itself or a second catnip plant.

8. The method of claim 7, further defined as comprising crossing said plant with a second, distinct catnip plant to produce an F1 hybrid catnip seed.

9. An F1 hybrid catnip seed produced by the method of claim 8.

10. A method of producing a catnip plant comprising a desired Z, E nepetalactone content comprising:
   (a) obtaining a plant according to claim 1,
   (b) applying plant breeding techniques to said plant and progeny thereof, and
   (c) selecting at least one further progeny plant resulting from said step (b) that comprises a desired Z, E nepetalactone content.

11. A composition comprising plant tissue of a catnip plant according to claim 1, wherein the catnip tissue comprises an elevated endogenous level of Z, E nepetalactone.

12. The plant of claim 1, further comprising a transgene.

13. A plant produced by introducing a single locus into catnip cultivar 'CR9', or a selfed progeny thereof comprising the single locus, wherein the single locus was introduced into catnip cultivar 'CR9' by crossing or genetic transformation and wherein a sample of seed of catnip cultivar 'CR9' has been deposited under ATCC Accession No. PTA-126211.

14. A seed that produces the plant of claim 13.

15. The method of claim 8, wherein the method further comprises:
   (a) crossing a plant grown from said F1 hybrid catnip seed with itself or a different catnip plant to produce a seed of a progeny plant of a subsequent generation;
   (b) growing a progeny plant of a subsequent generation from said seed of a progeny plant of a subsequent generation and crossing the progeny plant of a subsequent generation with itself or a second plant to produce a progeny plant of a further subsequent generation; and
   (c) repeating steps (a) and (b) using said progeny plant of a further subsequent generation from step (b) in place of the plant grown from said F1 hybrid catnip seed in step (a), wherein steps (a) and (b) are repeated with sufficient inbreeding to produce an inbred catnip plant.

16. A method of producing a commodity plant product comprising collecting the commodity plant product from the plant of claim 1.

17. The method of claim 16, wherein the commodity plant product is protein concentrate, protein isolate, grain, meal, flour, or oil.

18. A catnip commodity plant product produced by the method of claim 16, wherein the commodity plant product comprises at least one cell of catnip cultivar 'CR9', wherein a sample of seed of catnip cultivar 'CR9' has been deposited under ATCC Accession No. PTA-126211.

19. The plant of claim 6, wherein the endogenous essential oil profile further comprises about 3% 2-pinene, about 3.5% carophyllene, or less than 0.5% E, Z nepetalactone.

20. A method of extracting endogenous essential oil from a plant; wherein the method comprises:
   (a) cultivating a plant according to claim 1;
   (b) harvesting the plant; and
   (c) extracting the endogenous essential oil from the plant.

21. A commodity, industrial, or commercial product comprising at least a first cell of the plant of claim 1.

22. The product of claim 21, wherein the product is a toy, pet toy, herbal infusion, tea, nutrition product, or insect repellent.

23. The catnip plant of claim 1, wherein the catnip plant comprises an endogenous essential oil profile; and wherein the endogenous essential oil profile comprises at least about 75% Z, E nepetalactone.

* * * * *

UNITED STATES PATENT AND TRADEMARK OFFICE
CERTIFICATE OF CORRECTION

PATENT NO. : 10,602,702 B2
APPLICATION NO. : 15/338014
DATED : March 31, 2020
INVENTOR(S) : James E. Simon et al.

Page 1 of 1

It is certified that error appears in the above-identified patent and that said Letters Patent is hereby corrected as shown below:

In the Claims

Column 20, Line 65, please delete "cultivarl", and insert --cultivar--

Signed and Sealed this
Twenty-fourth Day of November, 2020

Andrei Iancu
*Director of the United States Patent and Trademark Office*